(12) United States Patent
Jeong et al.

(10) Patent No.: US 11,319,409 B2
(45) Date of Patent: May 3, 2022

(54) POLYIMIDE AND POLYIMIDE FILM, PREPARED THEREFROM, FOR FLEXIBLE DISPLAY

(71) Applicant: LG CHEM, LTD., Seoul (KR)

(72) Inventors: Hye Won Jeong, Daejeon (KR); Kichul Koo, Daejeon (KR); Kyungjun Kim, Daejeon (KR)

(73) Assignee: LG CHEM, LTD., Seoul (KR)

(*) Notice: Subject to any disclaimer, the term of this patent is extended or adjusted under 35 U.S.C. 154(b) by 64 days.

(21) Appl. No.: 16/461,601

(22) PCT Filed: Jan. 17, 2018

(86) PCT No.: PCT/KR2018/000810
§ 371 (c)(1),
(2) Date: May 16, 2019

(87) PCT Pub. No.: WO2018/143583
PCT Pub. Date: Aug. 9, 2018

(65) Prior Publication Data
US 2020/0062904 A1  Feb. 27, 2020

(30) Foreign Application Priority Data

Jan. 31, 2017 (KR) .................. 10-2017-0013726
Dec. 7, 2017 (KR) .................. 10-2017-0167165

(51) Int. Cl.
| | | |
|---|---|---|
| C08G 73/10 | (2006.01) | |
| C07C 211/56 | (2006.01) | |
| C07C 211/61 | (2006.01) | |
| C08J 5/18 | (2006.01) | |
| H01L 27/12 | (2006.01) | |
| H01L 51/00 | (2006.01) | |

(52) U.S. Cl.
CPC ........ *C08G 73/1067* (2013.01); *C07C 211/56* (2013.01); *C07C 211/61* (2013.01); *C08G 73/1007* (2013.01); *C08G 73/1042* (2013.01); *C08J 5/18* (2013.01); *H01L 27/1218* (2013.01); *H01L 51/0097* (2013.01); *C07C 2603/97* (2017.05); *C08J 2379/08* (2013.01); *H01L 2251/5338* (2013.01)

(58) Field of Classification Search
CPC ............ C08G 73/1067; C08G 73/1007; C08J 2379/08; C08L 79/08
See application file for complete search history.

(56) References Cited

U.S. PATENT DOCUMENTS

| | | |
|---|---|---|
| 9,434,816 B2 | 9/2016 | Park et al. |
| 9,447,241 B2 | 9/2016 | Jeong et al. |
| 10,059,805 B2 | 8/2018 | Jee et al. |
| 2013/0216803 A1 | 8/2013 | Sun et al. |
| 2014/0037930 A1 | 2/2014 | Sun et al. |
| 2014/0138669 A1 | 5/2014 | Nakagawa et al. |
| 2016/0096927 A1* | 4/2016 | Jee ................... C08G 73/1007 524/600 |

FOREIGN PATENT DOCUMENTS

| | | | |
|---|---|---|---|
| CN | 101591521 | * | 12/2009 |
| CN | 101591521 A | | 12/2009 |
| CN | 102492297 A | | 6/2012 |
| CN | 102585222 A | | 7/2012 |
| CN | 104066768 A | | 9/2014 |
| CN | 104540883 A | | 4/2015 |
| JP | 2004-182962 A | | 7/2004 |
| JP | 2005-262529 A | | 9/2005 |
| JP | 2006001968 | * | 1/2006 |
| KR | 10-2010-0080425 A | | 7/2010 |
| KR | 10-2012-0138991 A | | 12/2012 |
| KR | 10-2014-0054301 A | | 5/2014 |
| KR | 10-2014-0058550 A | | 5/2014 |
| KR | 10-2015-0007335 A | | 1/2015 |
| KR | 10-2016-0040123 A | | 4/2016 |
| TW | 201311780 A | | 3/2013 |
| TW | 201605978 A | | 2/2016 |

OTHER PUBLICATIONS

Zhang "Synthesis and characterization of bis(phenyl)fluorene based cardo polyimide membranes for H2/CH4 separation", J Mater Sci (2019) 54:10560-10569, published on Apr. 2019.*
Gaofenzi Huaxue Shiyan, (2012) vol. 2, p. 33, with English translation, 5 pages.
International Search Report and Written Opinion issued for PCT/KR2018/000810 dated Nov. 1, 2018, 9 pages.
P. Wen, et al., "Syntheses and Characterizations of Cardo Polyimides Based on New Spirobifluorene Diamine Monomer", Materials Chemistry and Physics, 2013, vol. 139, Nos. 2-3, pp. 923-930.
L.-Y. Lin et al., "A New Spirobifluorene-Bridged Bipolar System for a Nitric Oxide Turn-on Fluorescent Probe", Organic Letters, 2011, vol. 13, No. 9, pp. 2216-2219.
J. R. Weidman et al., "Structure Manipulation in Triptycene-based Polyimides through Main Chain Geometry Variation and Its Effect on Gas Transport Properties", Industrial & Engineering Chemistry Reserach, Jan. 30, 2017, vol. 56, No. 7, pp. 1868-1879.
Z. Wu et al., "Novel Soluble and Optically Active Polyimides Containing Axially Asymmetric 9,9'-spirobifluorene Units: Synthesis, Thermal, Optical and Chiral Properties", Polymer, 2012, vol. 53, No. 25, pp. 5706-5716.
D. S. Reddy et al., "Synthesis and Characterization of Soluble Poly(ether imide)s Based on 2,2'-bis(4-aminophenozy) 9,9'-spirobifluorene", Polymer, 2003, vol. 44, No. 3, p. 557 563.
Y. Zhuang et al., "Soluble, microporous, Tröger's Base copolyimides with tunable membrane performance for gas separation", Chem. Commun., 2016, vol. 52, pp. 3817-3820.

* cited by examiner

*Primary Examiner* — Gregory Listvoyb
(74) *Attorney, Agent, or Firm* — Rothwell, Figg, Ernst & Manbeck, P.C.

(57) ABSTRACT

Described is a polyimide prepared from a diamine containing a spiro or cardo group in a molecule structure, wherein the dimensional stability of the polyimide can be improved at a high temperature, and thus the polyimide can provide a polyimide film useful for a flexible substrate.

17 Claims, No Drawings

POLYIMIDE AND POLYIMIDE FILM, PREPARED THEREFROM, FOR FLEXIBLE DISPLAY

BACKGROUND OF THE INVENTION

1. Field of the Invention

This application is a 35 U.S.C. § 371 National Phase Entry Application from PCT/KR2018/000810, filed on Jan. 17, 2018, and designating the United States, which claims the benefit of priority to Korean Patent Application Nos. 10-2017-0013726, filed on Jan. 31, 2017 and 10-2017-0167165, filed on Dec. 7, 2017, the entire disclosures of which are incorporated herein by reference.

The present invention relates to a polyimide having improved heat resistance and thermal stability, and a polyimide film for a flexible display containing same.

2. Description of the Related Art

Polyimide (PI) is a polymer having a relatively low crystallinity or mostly amorphous structure. It is easy to be synthesized and prepared as a thin film. It is a polymer material having transparency, excellent heat resistance and chemical resistance due to a rigid chain structure, excellent mechanical and electrical properties and dimensional stability, as well as the advantage of not requiring a crosslinking group for curing. It is widely used in electric and electronic materials such as automotive, aerospace, flexible circuit boards, liquid crystal alignment films for LCD, adhesives and coatings.

However, although polyimide is a high-performance polymer material having high thermal stability, mechanical properties, chemical resistance, and electrical properties, it does not satisfy the colorless transparent property which is a basic requirement for use in the display field, and has a problem that the coefficient of thermal expansion should be further lowered. For example, Kapton commercially available from DuPont has a coefficient of thermal expansion as low as about 30 ppm/° C., but this value does not meet the requirements of plastic substrates. Therefore, many researches have been carried out to minimize changes in optical characteristics and thermal history while maintaining the basic characteristics of polyimide.

However, in order to be used in the display field, it is necessary to develop a polymer for a flexible display having a lower coefficient of thermal expansion and high solubility, transparency and thermal stability.

SUMMARY OF THE INVENTION

A problem to be solved by the present invention is to provide a polyimide having improved heat resistance and thermal stability.

Other problem to be solved by the present invention is to provide a polyimide film comprising the polyimide.

The present invention also provides a diamine having a novel structure comprising a spiro or cardo group in the molecular structure.

In order to solve the above-described problems, there is provided a polyimide produced from a polymerizable component comprising a tetracarboxylic dianhydride and at least one diamine selected from the following formulae 1a to 1e.

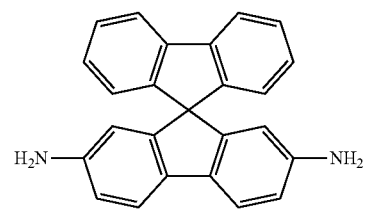
[Formula 1a]

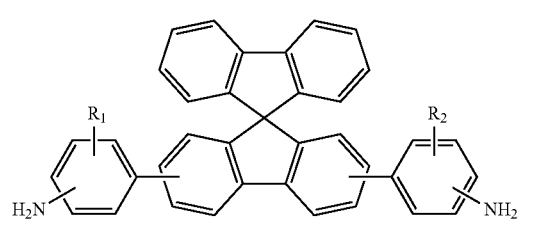
[Formula 1b]

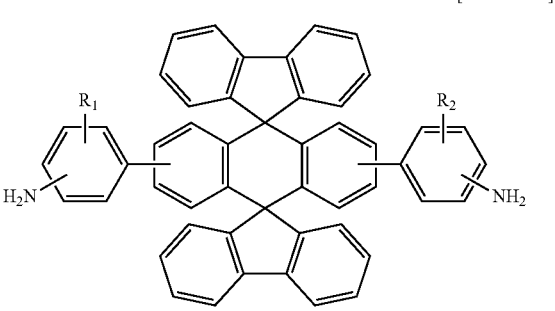
[Formula 1c]

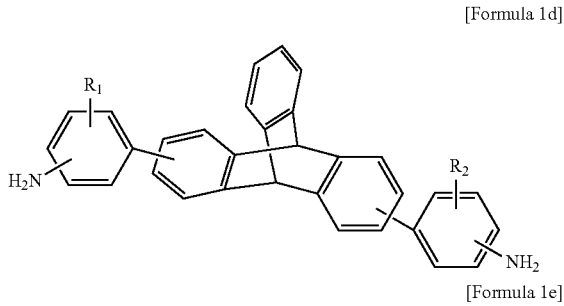
[Formula 1d]

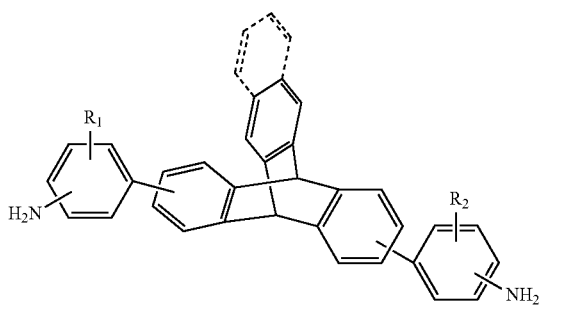
[Formula 1e]

In formulae 1b to 1e, $R_1$ and $R_2$ are each independently a hydrogen atom or a substituent selected from a halogen atom, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms. According to one embodiment, the diamine of formula 1 may be contained in an amount of 30 to 100 mol % based on the total content of the diamine.

According to one embodiment, the polyimide may have a coefficient of thermal expansion (CTE) of 50 ppm/° C. or less.

According to one embodiment, the polyimide may have a glass transition temperature (Tg) of 330° C. or higher.

In order to solve the other problems of the present invention, there is provided a polyimide film for a flexible display comprising the polyimide. The present invention also provides a diamine represented by any one of the following formulae 1a to 1e.

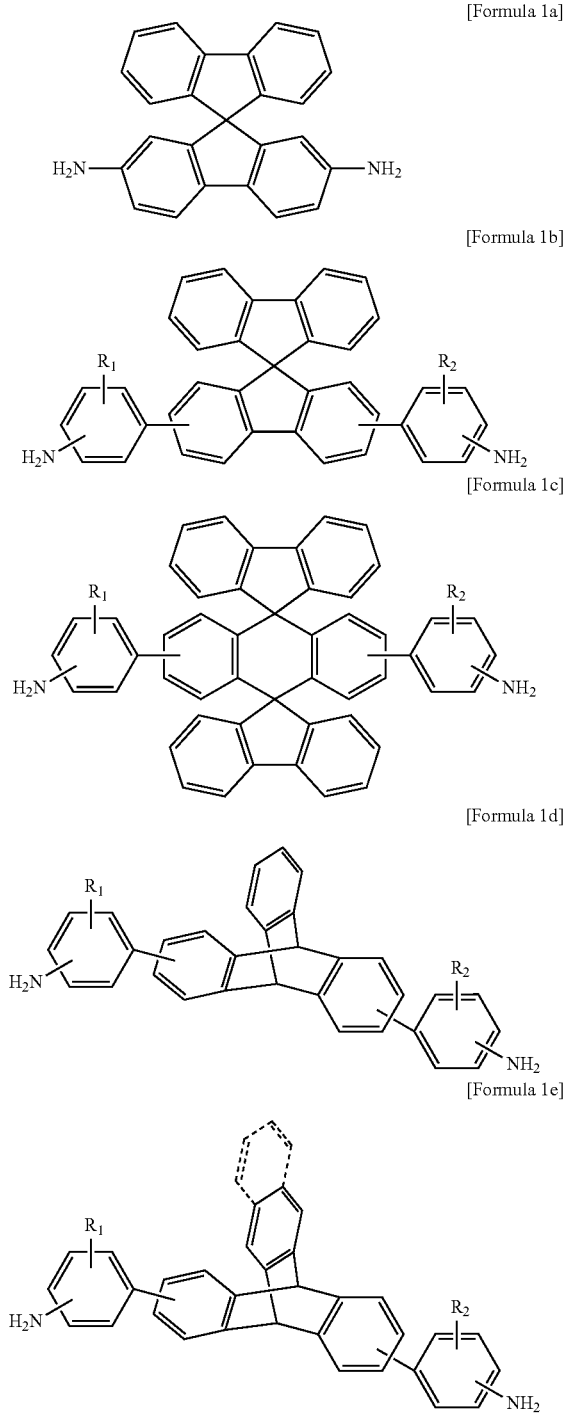

[Formula 1a]

[Formula 1b]

[Formula 1c]

[Formula 1d]

[Formula 1e]

In formulae 1b to 1e, $R_1$ and $R_2$ are each independently a hydrogen atom or a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms.

Effect of the Invention

The polyimide according to the present invention is produced from a diamine comprising a spiro or cardo group in which two or more phenyl groups are linked and fixed, and thus may have high glass transition temperature as well as improved dimensional stability against heat. The polyimide film produced from the polyimide according to the present invention is excellent in thermal stability so that it is suitable for a flexible device accompanied by a high temperature process, particularly an Oxide TFT (thin film transistor) and an OLED (organic light emitting diode) device using LTPS (low temperature polysilicon) process.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description, well-known functions or constructions are not described in detail if it is determined that they may obscure the gist of the present invention.

In the present disclosure, all the compounds or organic groups may be substituted or unsubstituted, unless otherwise specified. Herein, the term "substituted" means that at least one hydrogen contained in a compound or an organic group is substituted with a substituent selected from the group consisting of a halogen atom, an alkyl group having 1 to 10 carbon atoms, a halogenated alkyl group, a cycloalkyl group having 3 to 30 carbon atoms, an aryl group having 6 to 30 carbon atoms, a hydroxyl group, an alkoxy group having 1 to 10 carbon atoms, a carboxylic group, an aldehyde group, an epoxy group, a cyano group, a nitro group, an amino group, a sulfonic group or a derivative thereof.

In the present disclosure, unless otherwise specified, the term "a combination thereof" means two or more functional groups are bonded to each other via a linkage such as a single bond, a double bond, a triple bond, an alkylene group having 1 to 10 carbon atoms (e.g., a methylene group (—CH$_2$—) an ethylene group (—CH$_2$CH$_2$—), etc.), a fluoroalkylene group having 1 to 10 carbon atoms (e.g., a fluoromethylene group (—CF$_2$—), a perfluoroethylene group (—CF$_2$CF$_2$—), etc.), a hetero atom such as N, O, P, S or Si, or a functional group containing hetero atom (e.g., a heteroalkylene group containing a carbonyl group (—C(=O)—), an ether group (—O—), an ester group (—COO—), —S—, —NH— or —N=N—, etc. in the molecule), or two or more functional groups are condensed and linked.

A flexible device accompanied by a high temperature process is required to have high-temperature resistance.

Especially, for an Oxide TFT (thin film transistor) and an OLED (organic light emitting diode) device using LTPS (low temperature polysilicon) process, the process temperature is above 350° C. and may reach 500° C.

Even at this temperature, polyimides having excellent heat resistance are likely to be thermally decomposed and may undergo shrinkage or expansion due to heat. Therefore, in order to manufacture a flexible device, it is necessary to develop a polyimide which can exhibit excellent thermal stability while maintaining high transparency at high temperature, with excellent mechanical properties.

The present invention provides an ultrahigh heat resistant polyimide produced from a diamine having a novel structure.

Another object of the present invention is to provide a polyimide film comprising the polyimide.

The present invention provides a diamine represented by any one of the following formulae 1a to 1e.

[Formula 1a]

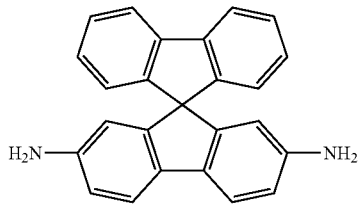

[Formula 1b]

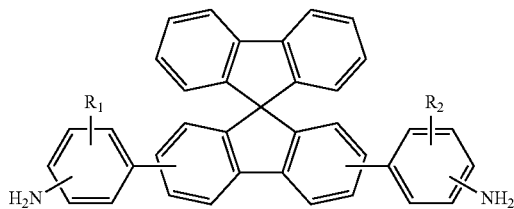

[Formula 1c]

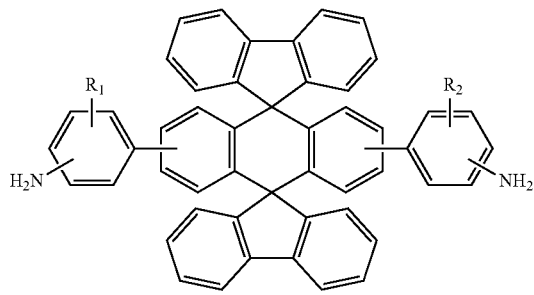

[Formula 1d]

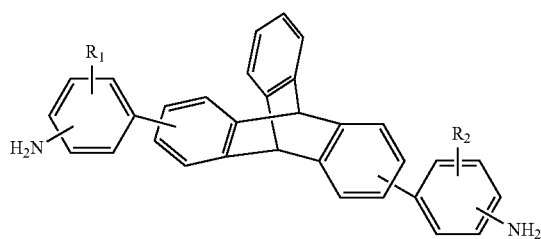

[Formula 1e]

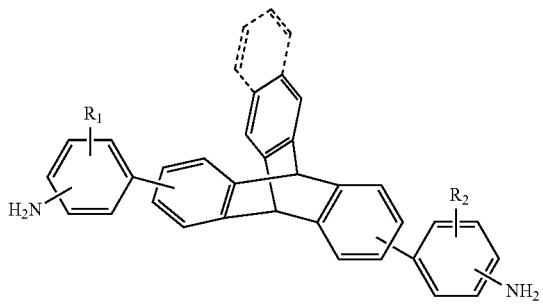

In formulae 1b to 1e, $R_1$ and $R_2$ are each independently a hydrogen atom or a substituent selected from a halogen atom, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms.

In addition, the present invention provides a polyimide produced from a polymerizable component comprising a tetracarboxylic dianhydride and at least one diamine, wherein the diamine is selected from the above formulae 1a to 1e.

According to one embodiment, the diamine of formula 1 may be contained in an amount of 30 to 100 mol %, preferably 50 to 100 mol %, based on the total content of diamine of the polymerizable component.

The diamine according to the present invention has a structure including a spiro or cardo group in which two or more phenyl groups are linked and fixed. In the case of the polyimide including the group in which the phenyl groups are not fixed, the glass transition temperature is elevated but the CTE (coefficient of thermal expansion) is increased to cause the reduced thermal stability. However, in the present invention, by fixing the phenyl groups, it is possible to provide polyimide having a high glass transition temperature and a less increased CTE and thus excellent thermal stability.

According to one embodiment, the glass transition temperature of the polyimide may be 330° C. or higher, and preferably 350° C. or higher.

According to one embodiment, the CTE of the polyimide may be 50 ppm/° C. or less, preferably 30 ppm/° C. or less, for example, 10 to 30 ppm/° C.

At this time, a sample having a thickness of 10 μm, a width of 5 mm and a length of 5 cm is set so as to be pulled with a force of 0.02 N after being fixed with a jig to have a measuring length of 16 mm, and the temperature is raised to 300° C. at a rate of 5° C./min (first heating), then lowered to 50° C. (first cooling) and again raised to 450° C. (second heating). The CTE is a value measured in the range of 100 to 250° C.

According to one embodiment, it is preferable that the molar ratio of the total content of the tetracarboxylic dianhydride to the content of the diamine is 1:0.99 to 0.99:1, preferably 1:0.98 to 0.98:1.

The tetracarboxylic dianhydride may be used as long as it is generally used for the production of polyimide. For example, the tetracarboxylic dianhydride which can be used for the production of polyimide may be a teteracarboxylic dianhydride comprising a tetravalent aromatic, alicyclic or aliphatic organic group or a combination thereof in the molecule, wherein the tetravalent aliphatic, alicyclic or aromatic organic groups are linked each other via a cross-linkage. For example, it may be a tetracarboxylic dianhydride comprising a tetravalent organic structure selected from the group consisting of tetravalent organic groups represented by the following formulae (2a) to (2e) and a combination thereof.

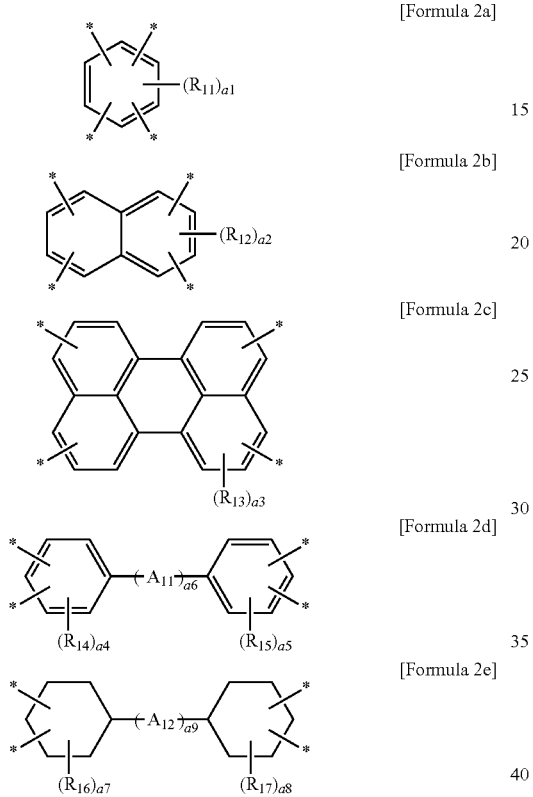

In formulae 2a to 2e, $R_{11}$ to $R_{17}$ may be each independently a hydrogen atom or a substituent selected from a halogen atom (selected from —F, —Cl, —Br and —I), a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, a1 may be an integer of 0 to 2, a2 may be an integer of 0 to 4, a3 may be an integer of 0 to 8, a4 and a5 may be each independently an integer of 0 to 3, a6 and a9 may be each independently an integer of 0 to 3, and a7 and a8 may be each independently an integer of 0 to 9, and $A_{11}$ and $A_{12}$ may be each independently selected from the group consisting of a single bond, —O—, —CR$_{18}$R$_{19}$—, —C(=O)—, —C(=O)NH—, —S—, —SO$_2$—, a phenylene group and a combination thereof, wherein R$_{18}$ and R$_{19}$ may be each independently selected from the group consisting of a hydrogen atom, an alkyl group having 1 to 10 carbon atoms, and a fluoroalkyl group having 1 to 10 carbon atoms.

For example, the tetracarboxylic dianhydride to be used in the present invention may include, but is not limited to, tetracarboxylic dianhydride containing a tetravalent organic group selected from the group consisting of the following formulae 3a to 3r in the structure.

(3a)

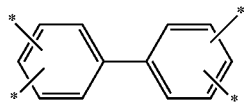

(3b)

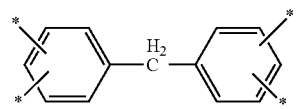

(3c)

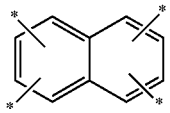

(3d)

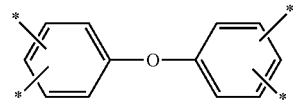

(3e)

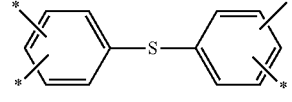

(3f)

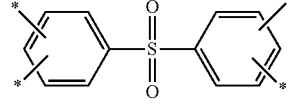

(3g)

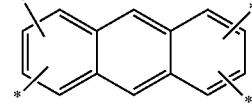

(3h)

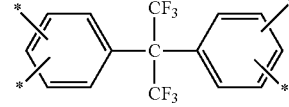

(3i)

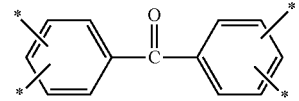

(3j)

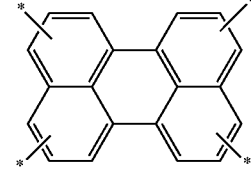

(3k)

-continued

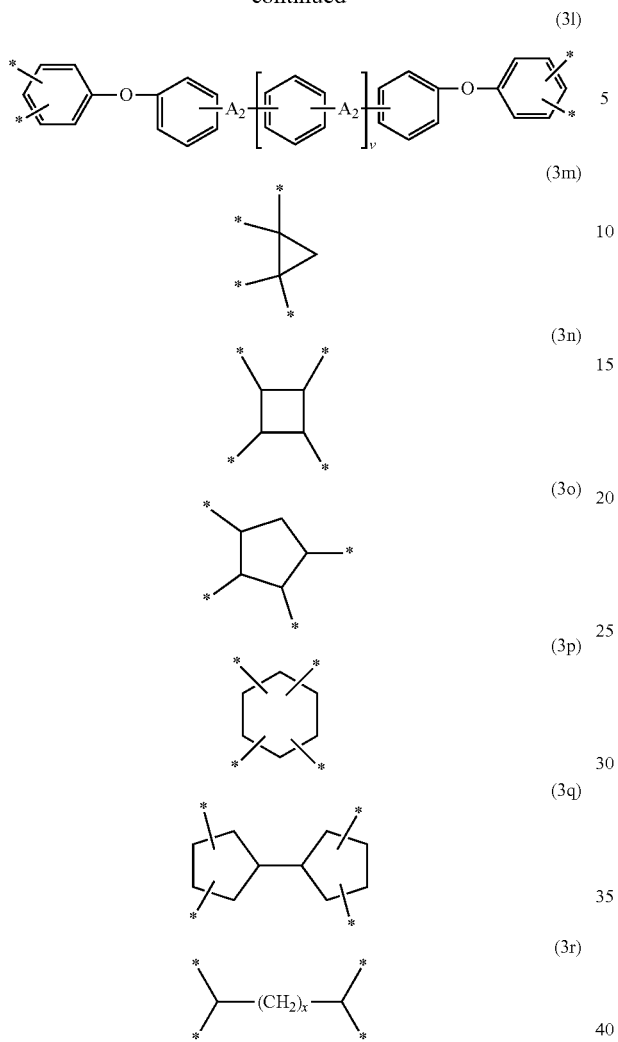

In formula 3l, $A_2$ may be selected from the group consisting of a single bond, —O—, —C(=O)—, —C(=O)NH—, —S—, —SO$_2$—, a phenylene group and a combination thereof and v is an integer of 0 or 1, and in formula 3r, x is an integer of 1 to 10.

In addition, at least one hydrogen atom present in the tetravalent organic group of formulae 3a to 3r may be substituted with a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms.

In the present invention, other diamines than the diamine of the above formula 1 may also be used. The diamine may be used as long as it is generally used for the production of polyimide. Specifically, the diamine may be a diamine comprising a divalent aliphatic, alicyclic or aromatic organic group, or a combination thereof, wherein the divalent aliphatic, alicyclic or aromatic organic groups may be directly linked each other, or may be linked each other via a crosslinkage. For example, it may be a diamine comprising a divalent organic group selected from the group consisting of divalent organic groups represented by the following formulae 4a to 4c, and a combination thereof.

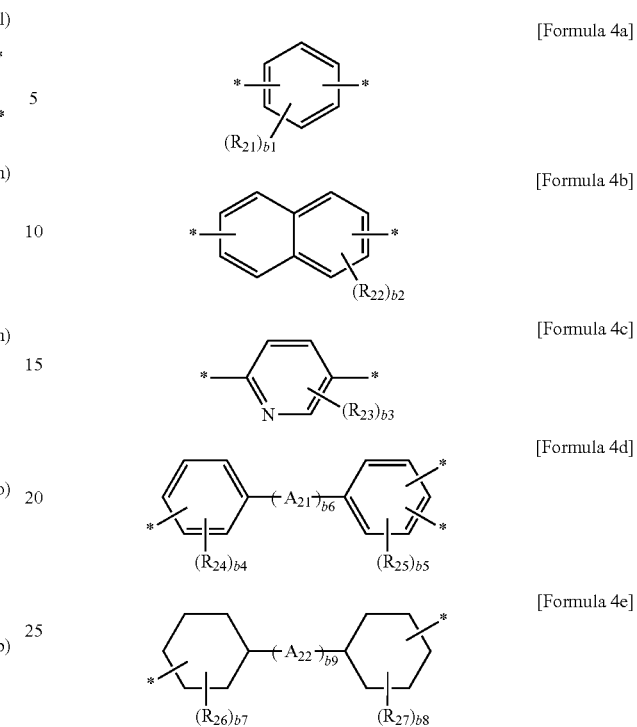

In formulae 4a to 4e, $R_{21}$ to $R_{27}$ may be each independently selected from an alkyl group having 1 to 10 carbon atoms (e.g., a methyl group, an ethyl group, a propyl group, an isopropyl group, an n-butyl group, a tert-butyl group, a pentyl group, etc.), a halogen group, a hydroxy group, a carboxyl group, an alkoxy group having 1 to 10 carbon atoms (e.g., a methoxy group, an ethoxy group, a propoxy group, a tert-butoxy group, etc.) and a fluoroalkyl group having 1 to 10 carbon atoms (e.g., a trifluoromethyl group, etc.), $A_{21}$ and $A_{22}$ may be each independently selected from a single bond, —O—, —CR'R"—(wherein R' and R" are each independently selected from a hydrogen atom, an alkyl group having 1 to 10 carbon atoms (e.g., a methyl group, an ethyl group, a propyl group, an isopropyl group, an n-butyl group, a tert-butyl group, a pentyl group, etc.) and a haloalkyl group having 1 to 10 carbon atoms (e.g., a trifluoromethyl group, etc.)), —(C=O)—, —(C=O)O—, —(C=O)NH—, —S—, —SO—, —SO$_2$—, —O[CH$_2$CH$_2$O]y (wherein y is an integer of 1 to 44), —NH(C=O)NH—, —NH(C=O)O—, a monocyclic or polycyclic cycloalkylene group having 6 to 18 carbon atoms (e.g., a cyclohexylene group, etc.), a monocyclic or polycyclic arylene group having 6 to 18 carbon atoms (e.g., a phenylene group, a naphthalene group, a fluorenylene group, etc.), and a combination thereof, and $b_1$, $b_4$ and $b_5$ are each independently an integer of 0 to 4, $b_2$ is an integer of 0 to 6, $b_3$ is an integer of 0 to 3, $b_6$ and $b_9$ are each independently an integer of 0 or 1, and $b_7$ and $b_8$ are each independently an integer of 0 to 10.

For example, the diamine to be used in the present invention may include, but is not limited to, a diamine containing a divalent organic group selected from the group consisting of the following formulae 5a to 5t in the structure.

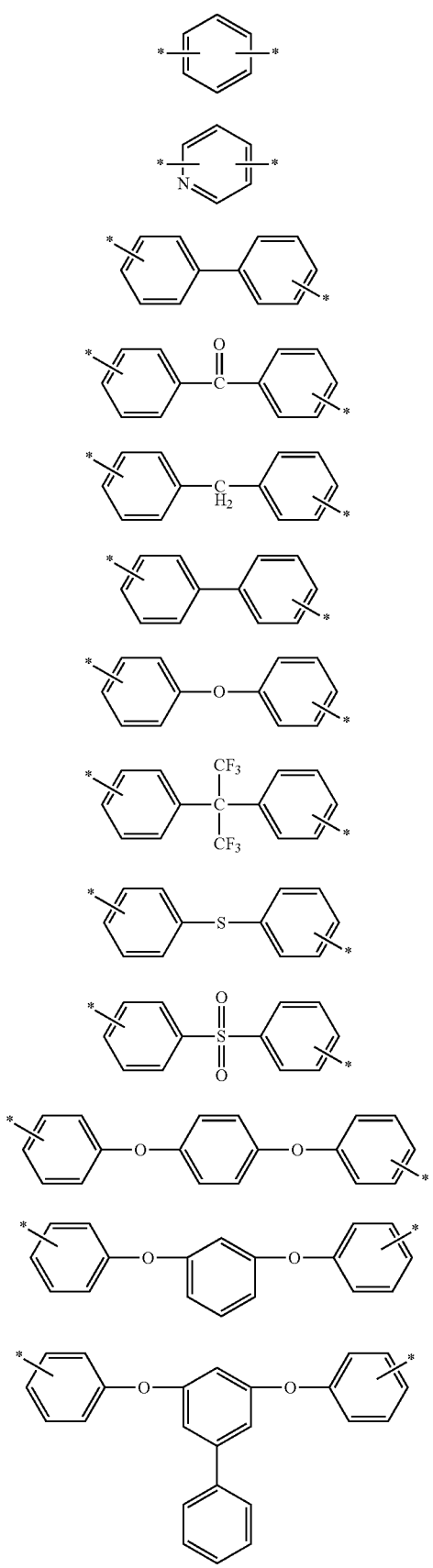

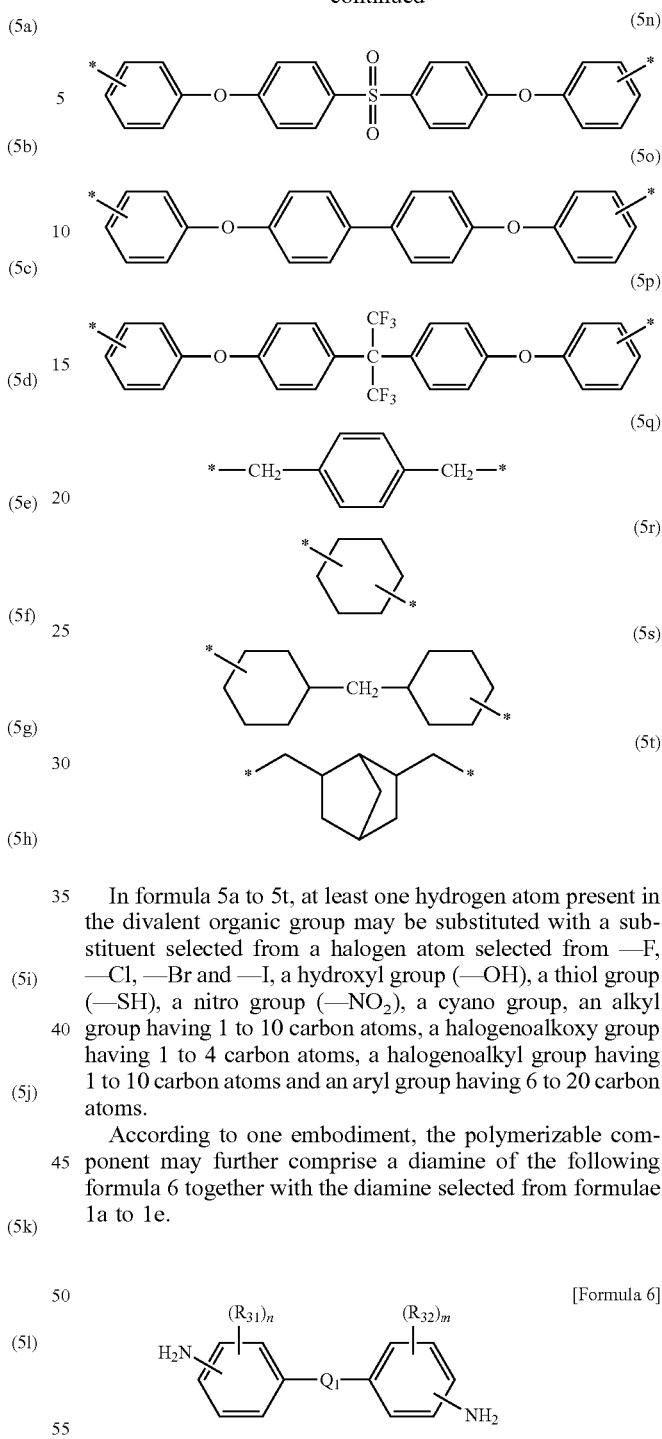

In formula 5a to 5t, at least one hydrogen atom present in the divalent organic group may be substituted with a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms.

According to one embodiment, the polymerizable component may further comprise a diamine of the following formula 6 together with the diamine selected from formulae 1a to 1e.

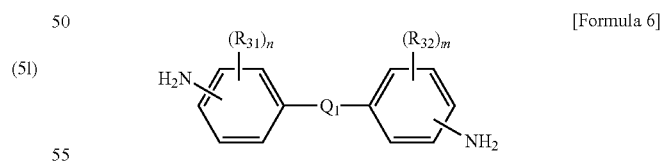

In formula 6,

R$_{31}$ and R$_{32}$ are each independently a substituent selected from a halogen atom selected from —F, —Cl, —Br and —I, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, n and m are each independently an integer of 0 to 4, and Q$_1$ is selected from the group consisting of a single bond, —O—, —CR$_{18}$R$_{19}$—, —(C═O)—, —(C═O)O—, —(C=O)NH—, —S—, —SO$_2$—, a phenylene group and a combination thereof, wherein R$_{18}$ and R$_{19}$ are each independently selected from the group consisting of a hydrogen atom, an alkyl group having 1 to 10 carbon atoms, and a fluoroalkyl group having 1 to 10 carbon atoms.

The reaction of the tetracarboxylic dianhydride with the diamine can be carried out according to a conventional method for producing a polyimide precursor such as solution polymerization. Specifically, a diamine is dissolved in an organic solvent, and then a tetracarboxylic dianhydride is added to the resulting mixed solution to cause a polymerization reaction to produce a polyamic acid which is a polyimide precursor.

The reaction can be carried out under an inert gas or a nitrogen stream and can be carried out under anhydrous conditions.

The polymerization reaction may be carried out at a temperature of −20 to 60° C., preferably 0 to 45° C. If the reaction temperature is too high, the reactivity may become high, the molecular weight may become large, and the viscosity of the precursor composition may increase, which may be disadvantageous in terms of the process.

Specifically, the organic solvent that can be used in the polymerization reaction may be selected from the group consisting of ketones such as y-butyrolactone, 1,3-dimethyl-imidazolidinone, methyl ethyl ketone, cyclohexanone, cyclopentanone and 4-hydroxy-4-methyl-2-pentanone; aromatic hydrocarbons such as toluene, xylene and teteramethylbenzene; glycol ethers (Cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, ethanol, propanol, ethylene glycol, propylene glycol, carbitol, dimethylacetamide (DMAc), N,N-diethylacetamide, dimethylformamide (DMF), diethylformamide (DEF), N-methylpyrrolidone (NMP), N-ethylpyrrolidone (NEP), 1,3-dimethyl-2-imidazolinone, N,N-dimethylmethoxyacetamide, dimethylsulfoxide, pyridine, dimethylsulfone, hexamethylphosphoramide, tetramethylurea, N-methylcaprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether and a mixture thereof.

Preferably, the organic solvent may include a sulfoxide-based solvent such as dimethyl sulfoxide and diethyl sulfoxide, a formamide-based solvent such as N,N-dimethylformamide and N,N-diethylformamide, an acetamide-based solvent such as N,N-dimethylacetamide and N,N-diethylacetamide, a pyrrolidone-based solvent such as N-methyl-2-pyrrolidone and N-vinyl-2-pyrrolidone, a phenol-based solvent such as phenol, o-, m- or p-cresol, xylenol, halogenated phenol and catechol, or hexamethylphosphoramide, y-butyrolactone or the like, and these solvent may be used alone or as mixture. More preferably, it may be selected from N,N-diethylacetamide (DEAc), N,N-diethylformamide (DEF), N-ethylpyrrolidone (NEP) or a mixture thereof.

According to one embodiment, the organic solvent may further include aromatic hydrocarbons such as xylene and toluene. Also, in order to promote the dissolution of the polymer, about 50% by weight or less of an alkali metal salt or alkaline earth metal salt may be further added to the solvent, based on the total amount of the solvent.

The polyimide precursor solution prepared according to the above-described production method preferably contains a solid content in an amount such that the composition has an appropriate viscosity in consideration of processability such as coating property during a film forming process. According to one embodiment, the content of the composition can be adjusted so that total content of the polyimide precursor is 5 to 20 wt %, preferably 8 to 18 wt %, more preferably 8 to 12 wt %.

The polyimide precursor solution may be adjusted to have a viscosity of 2,000 cP or more, or 3,000 cP or more, and the viscosity of the polyimide precursor solution is 10,000 cP or less, preferably 9,000 cP or less, more preferably 8,000 cP or less. If the viscosity of the polyimide precursor solution exceeds 10,000 cP, the efficiency of defoaming at the time of processing the polyimide film is lowered. As a result, the produced film has not only poor process efficiency but also poor surface roughness due to bubbling, so that the electrical, optical and mechanical properties can be degraded.

The polyimide according to the present invention may have a weight average molecular weight of 10,000 to 200,000 g/mol, or 20,000 to 100,000 g/mol, or 30,000 to 100,000 g/mol. The molecular weight distribution (Mw/Mn) of the polyimide according to the present invention is preferably 1.1 to 2.5. If the weight average molecular weight or the molecular weight distribution of the polyimide is out of the above range, film formation may be difficult or the properties of the polyimide-based film such as transparency, heat resistance, and mechanical properties may deteriorate.

Next, the polyimide precursor obtained as a result of the polymerization reaction is imidized to prepare a transparent polyimide film. Specifically, the imidization process may be a chemical imidization or thermal imidization process.

For example, a dehydrating agent and an imidization catalyst are added to the polymerized polyimide precursor solution, then the polyimide precursor solution is heated at a temperature of 50 to 100° C. and imidized by a chemical reaction, or imidized by removing alcohol from the solution under reflux, to obtain a polyimide.

In the chemical imidization method, pyridine, triethylamine, picoline or quinoline may be used as the imidization catalyst. In addition, as the imidization catalyst, a substituted or unsubstituted nitrogen-containing heterocyclic compound, a N-oxide compound of a nitrogen-containing heterocyclic compound, a substituted or unsubstituted amino acid compound, an aromatic hydrocarbon compound having a hydroxyl group, or an aromatic heterocyclic compound may be used. In particular, lower alkyl imidazole, such as 1,2-dimethylimidazole, N-methylimidazole, N-benzyl-2-methylimidazole, 2-methylimidazole, 2-ethyl-4-methylimidazole and 5-methylbenzimidazole, isoquinoline, substituted pyridine, such as 3,5-dimethylpyridine, 3,4-dimethylpyridine, 2,5-dimethylpyridine, 2,4-dimethylpyridine and 4-n-propylpyridine, p-toluenesulfonic acid and the like may also be used.

As the dehydrating agent, an acid anhydride such as acetic anhydride may be used.

Alternatively, imidization can be carried out by applying the polyimide precursor solution onto a substrate and then heat treating it.

The polyimide precursor solution may be in the form of a solution dissolved in an organic solvent. In case of solution form, for example, when the polyimide precursor is synthesized in an organic solvent, the solution may be the reaction solution itself, or the solution may be obtained by diluting the reaction solution with another solvent. When the polyimide precursor is obtained as a solid powder, it may be dissolved in an organic solvent to form a solution.

The present invention provides a method for producing a polyimide film, comprising the steps of:
applying a polyimide precursor solution onto a substrate; and
heat treating the applied polyimide precursor solution.

The polyimide precursor solution is applied on a substrate and heat treated in an IR oven, in a hot air oven or on a hot plate. The heat treatment temperature may range from 300 to 500° C., preferably from 320 to 480° C. It may be performed in a multi-stage heating process within the above temperature range. The heat treatment process may be performed for 20 to 70 min, and preferably for 20 to 60 min.

The organic solvent contained in the polyimide precursor solution of the present invention may be the same as the organic solvent used in the synthesis reaction.

In the present invention, a silane coupling agent, a cross-linkable compound, an imidization promoter for efficiently advancing imidization, and the like may be added, provided that the effect of the invention is not impaired. The polyimide film may have a haze of 1 or less, preferably 0.9 or less, or 0.7 or less, more preferably 0.5 or less, to provide a polyimide film with improved transparency. At this time, a thickness of the polyimide film may be 8 to 15 μm, preferably 10 to 12 μm.

Also, it may be a colorless transparent polyimide film having a transmittance to light at a wavelength of 380 to 760 nm is 80% or more and a yellowness index (YI) of 25 or less, preferably about 20 or less, more preferably about 16 or less, or 15 or less in a film thickness range of 5 to 30 μm. The polyimide film can exhibit significantly improved transparency and optical characteristics due to excellent light transmittance and yellowness index as described above.

The polyimide film has an in-plane retardation value ($R_{in}$) of about 0 to 100 nm and an absolute value of a thickness retardation value ($R_{th}$) of about 1500 nm or less, or 0 to 1000 nm or less, preferably 30 to 800 nm or less, more preferably 50 to 700 nm or less. In the above range of the thickness retardation, it is possible to exhibit suitable visual sensibility for display. When the thickness retardation value is 1500 nm or more, a phase difference is generated in the polyimide film, and the light is distorted, so that the visual sensibility can be remarkably lowered.

In another embodiment of the present invention, there is provided a molded article comprising the polyimide copolymer.

The molded article may be a film, a fiber, a coating material, an adhesive material, or the like, but is not limited thereto. The molded article may be formed by a dry-wet method, a dry method, a wet method, or the like using a composite composition of the copolymer and the inorganic particles, but is not limited thereto. Specifically, as described above, the molded article may be an optical film. In this case, the article can be easily produced by applying the composition comprising the polyimide copolymer onto a substrate by a method such as spin coating, and then drying and curing it.

The polyimide according to the present invention can exhibit excellent heat resistance against heat change that may occur during a high-temperature process, and therefore it can be used in various fields such as a substrate for a device, a cover substrate for a display, an optical film, an IC (integrated circuit) package, an adhesive film, a multilayer flexible printed circuit (FPC), a tape, a touch panel, a protective film for an optical disc, and the like.

According to another embodiment of the present invention, there is provided a display device comprising the molded article. Specifically, the display device may include a liquid crystal display device (LCD), an organic light emitting diode (OLED), and the like. Particularly, it may be suitable for an OLED device using a low temperature polysilicon (LTPS) process that requires a high temperature process, but is not limited thereto.

Hereinafter, embodiments of the present invention will be described in detail so that those skilled in the art can easily carry out the present invention. The present invention may, however, be embodied in many different forms and should not be construed as limited to the embodiments set forth herein.

SYNTHESIS EXAMPLE 1

The diamine compound of Formula 10 (Compound 10) was prepared as follows.

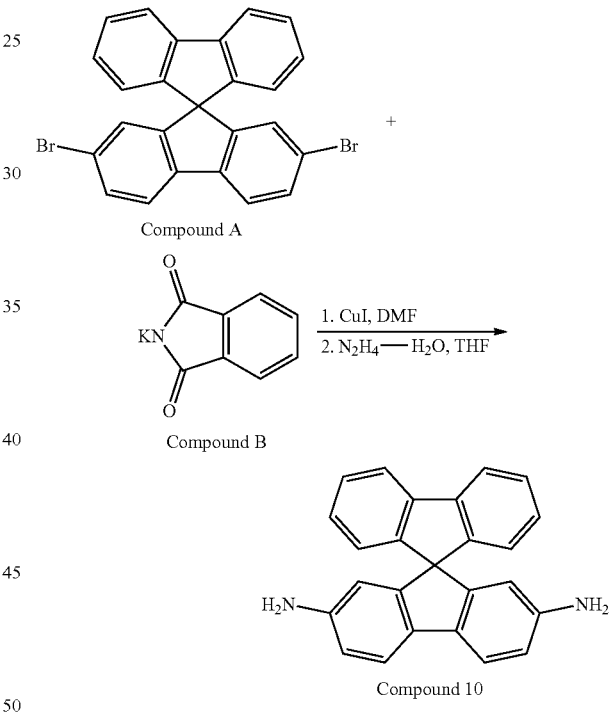

Compound A (20.0 g, 42.4 mmol) and Compound B (15.7 g, 84.8 mmol) were dispersed in dimethylformaldehyde (200 ml) and copper iodide (1.6 g, 8.5 mmol) was added and heated with stirring for 12 hours. When the reaction was completed, the temperature was lowered to room temperature, and the solid obtained by filtration was extracted with chloroform and the filtrate was concentrated to prepare an intermediate. The intermediate was completely dissolved in tetrahydrofuran (100 ml), and an aqueous hydrazine solution (10 ml) was added thereto, followed by heating and stirring for 1 hour. When the reaction was completed, the temperature was lowered to room temperature, and the filtrate obtained by filtration was added to water (250 mL) to form a precipitate. It was filtered to give the compound of formula 10 (7.2 g, yield 49%). MS[M+H]$^+$=347

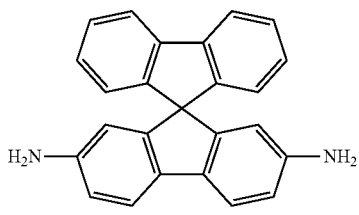

SYNTHESIS EXAMPLE 2

The diamine compound of Formula 11 (Compound 11) was prepared as follows.

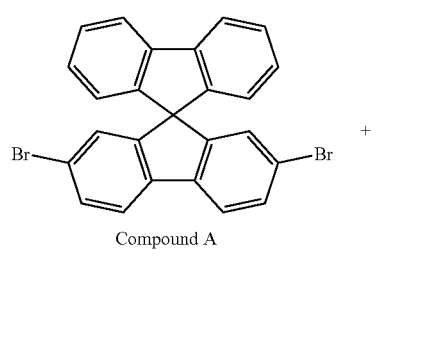

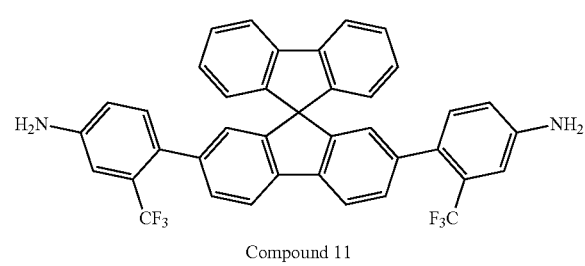

Compound A (30.0 g, 63.6 mmol) and Compound C (30.7 g, 127.2 mmol) were completely dissolved in tetrahydrofuran (300 ml), and then 1.5 M aqueous potassium carbonate solution (150 ml) was added. Tetrakistriphenylphosphinopalladium (1.24 g, 1.08 mmol) was added thereto, followed by heating and stirring for 4 hours. When the reaction was completed, the temperature was lowered to room temperature, and the solid obtained by filtration was washed with water (300 mL) and ethanol (300 ml) to give the compound of formula 11 (20.0 g, yield 91%). MS[M+H]$^+$=347

SYNTHESIS EXAMPLE 3

The diamine compound of Formula 12 (Compound 12) was prepared as follows.

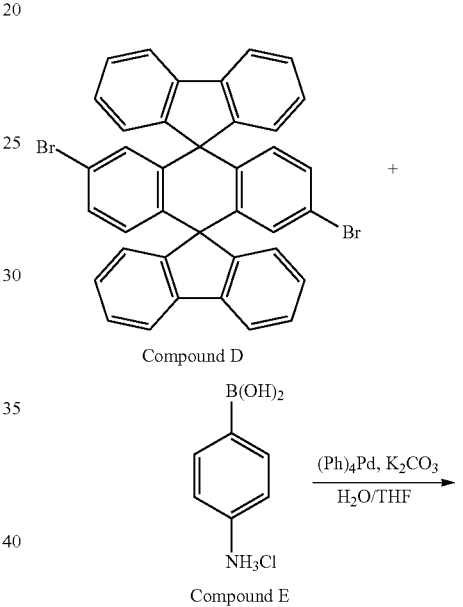

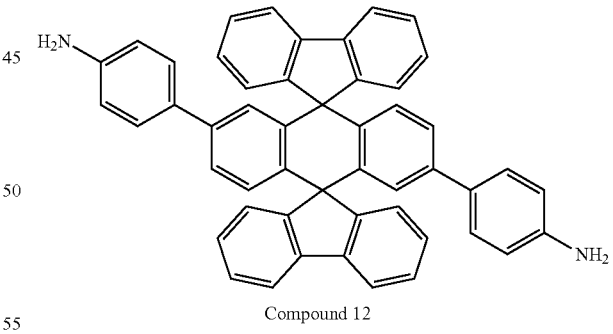

Compound D (30.0 g, 47.2 mmol) and compound E (16.3 g, 94.4 mmol) were completely dissolved in tetrahydrofuran (250 ml), and then 1.5 M aqueous potassium carbonate solution (100 ml) was added. Tetrakistriphenylphosphinopalladium (1.0 g, 0.87 mmol) was added thereto, followed by heating and stirring for 4 hours. When the reaction was completed, the temperature was lowered to room temperature, and the solid obtained by filtration was washed with water (200 mL) and ethanol (200 ml) to give the compound of formula 12 (30.3 g, yield 97%). MS[M+H]$^+$=663

[Formula 12]

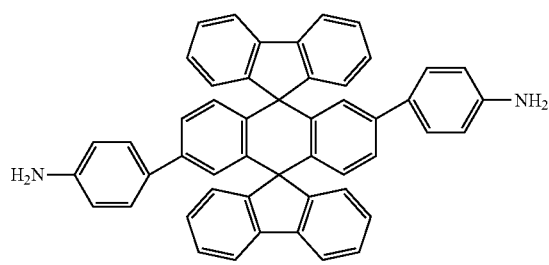

EXAMPLE 1

On one side of the alkali-free glass as a carrier substrate, a composition comprising 20% by weight of a polyamic acid resin obtained by polymerizing 1 mol of BPDA (3,3,4,4'-biphenyltetracarboxylic dianhydride), 0.5 mol of TFDB (2,2'-bis(trifluoromethyl)-[1,1'-biphenyl]-4,4'-diamine) and 0.5 mol of the diamine of formula 10 prepared in Synthesis Example 1 and 80% by weight of DMAc (dimethylacetamide) as a solvent was applied to a thickness of 10 μm after drying. The resulting coating was continuously subjected to a drying step at 100° C. and a curing step at 300° C. for 60 minutes to form a polyimide film for forming a polymer layer of a flexible substrate.

EXAMPLE 2

On one side of the alkali-free glass as a carrier substrate, a composition comprising 20% by weight of a polyamic acid resin obtained by polymerizing 1 mol of BPDA and 0.99 mol of the diamine of formula 11 prepared in Synthesis Example 2 and 80% by weight of DMAc as a solvent was applied to a thickness of 10 μm after drying. The resulting coating was continuously subjected to a drying step at 100° C. and a curing step at 300° C. for 60 minutes to form a polyimide film for forming a polymer layer of a flexible substrate.

EXAMPLE 3

On one side of the alkali-free glass as a carrier substrate, a composition comprising 20% by weight of a polyamic acid resin obtained by polymerizing 1 mol of BPDA, 0.5 mol of TFDB and 0.5 mol of the diamine of formula 12 prepared in Synthesis Example 3 and 80% by weight of DMAc as a solvent was applied to a thickness of 10 μm after drying. The resulting coating was continuously subjected to a drying step at 100° C. and a curing step at 300° C. for 60 minutes to form a polyimide film for forming a polymer layer of a flexible substrate.

COMPARATIVE EXAMPLE 1

On one side of the alkali-free glass as a carrier substrate, a composition comprising 20% by weight of a polyamic acid resin obtained by polymerizing 1 mol of BPDA and 0.99 mol of TFDB and 80% by weight of DMAc as a solvent was applied to a thickness of 10 μm after drying. The resulting coating was continuously subjected to a drying step at 100° C. and a curing step at 300° C. for 60 minutes to form a polyimide film for forming a polymer layer of a flexible substrate containing the polyimide resin.

COMPARATIVE EXAMPLE 2

A polyimide film for forming a polymer layer of a flexible substrate was produced in the same manner as in Example 1, except that diamine (SBF) represented by the following formula was used.

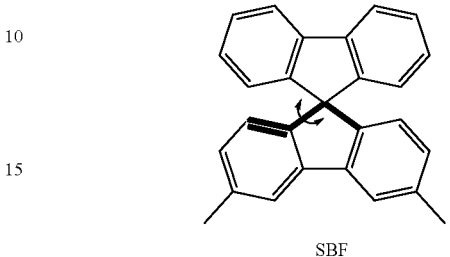

SBF

The coefficient of thermal expansion (CTE), the glass transition temperature (Tg) and the thickness retardation ($R_{th}$) of the films prepared in Examples 1 to 3 and Comparative Examples 1 and 2 were evaluated as follows and the results are shown in Table 1.

1) Coefficient of Thermal Expansion (CTE) and Glass Transition Temperature (Tg)

A sample having a thickness of 10 μm, a width of 5 mm and a length of 5 cm was set to be pulled by a force of 0.02 N after being fixed with a jig to have a measuring length of 16 mm, and the temperature was raised to 300° C. at a rate of 5° C./min (first heating), then lowered to 50° C. (first cooling) and again raised to 450° C. (second heating). The thermal expansion value in the 100-250° C. was measured by TMA (Q400 manufactured by TA instruments). The inflection point shown in the temperature raising section of the first heating step was defined as Tg.

2) Retardation ($R_{th}$)

The thickness retardation ($R_{th}$) of the film having a thickness of 10 μm, a width of 5 cm and a length of 5 cm was measured by Axoscan.

TABLE 1

| | CTE (ppm/° C., 100~250° C. @ $2^{nd}$ heat) | Tg (° C.) | $R_{th}$ (@ 550 nm) |
|---|---|---|---|
| Example 1 | 36.3 | 363 | −299 |
| Example 2 | 50 | 363 | −200 |
| Example 3 | 26.8 | >450 | −657 |
| Comparative Example 1 | 51 | 318 | −915 |
| Comparative Example 2 | 55 | 350 | −180 |

From the results shown in Table 1, it can be seen that the polyimide film according to the present invention has a lower CTE value and a higher glass transition temperature than the polyimides of Comparative Examples 1 and 2. In particular, in the case of Example 2, CTE value is similar to that in Comparative Example 1, but the glass transition temperature is much higher. According to the present invention, by including a spiro or cardo group in which two or more phenyl groups are linked and fixed, the movement of the phenyl group can be restricted even when the temperature rises, and the dimensional stability against heat can be further improved.

Compared with Comparative Example 2, it can be seen that the diamine according to the present invention has a linear structure, so that the Tg can be increased while minimizing the CTE increase compared with the conventional cardo monomer.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

What is claimed is:

1. A polyimide comprising a polymerized and imidized product of a composition comprising a tetracarboxylic dianhydride and a diamine that is selected from the following formulae 1b to 1e,

[Formula 1b]

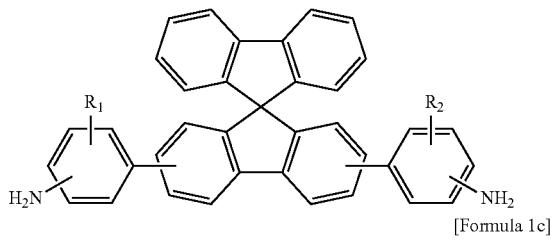

[Formula 1c]

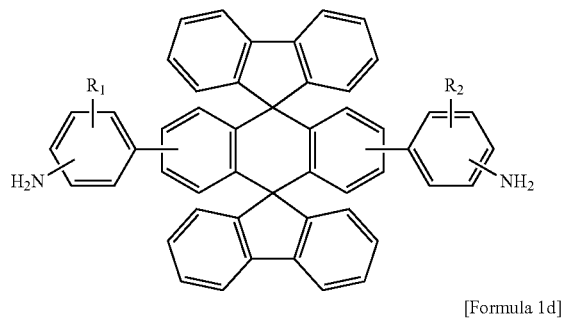

[Formula 1d]

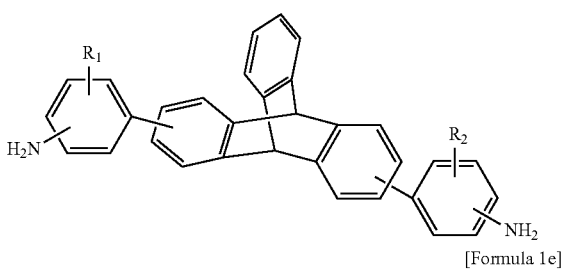

[Formula 1e]

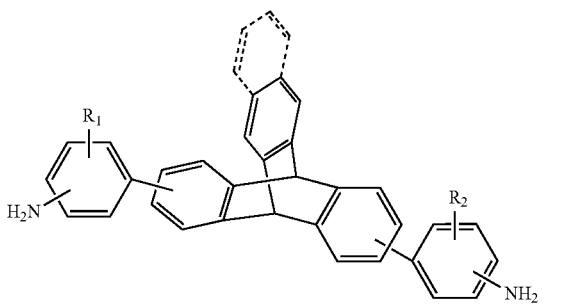

wherein, in formulae 1c to 1e,
R$_1$ and R$_2$ are each independently a hydrogen atom or a substituent selected from a halogen atom, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, and wherein in Formula 1b, R$_1$ and R$_2$ are each independently a halogenoalkyl group having 1 to 10 carbon atoms.

2. The polyimide according to claim 1, wherein the composition comprises the diamine selected from formulae 1b to 1e in an amount of 30 to 100 mol % based on the total content of the diamine.

3. The polyimide according to claim 1, wherein a coefficient of thermal expansion (CTE) is 50 ppm/° C. or less as measured in the range of 100 to 250° C.

4. The polyimide according to claim 1, wherein a glass transition temperature (Tg) is 330° C. or higher.

5. The polyimide according to claim 1, wherein the composition further comprises the diamine of formula 6,

[Formula 6]

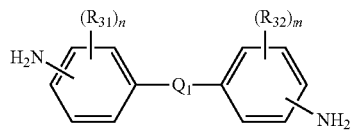

wherein, in formula 6,
R$_{31}$ and R$_{32}$ are each independently selected from a hydrogen atom, a halogen atom, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, n and m are each independently an integer of 0 to 4, and Q$_1$ is selected from the group consisting of a single bond, —O—, —CR$_{18}$R$_{19}$-, —C(=O)—, —C(=O)O—, —C(=O)NH—, —S—, —SO$_2$-, a phenylene group and a combination thereof, wherein R$_{18}$ and R$_{19}$ are each independently selected from the group consisting of a hydrogen atom, an alkyl group having 1 to 10 carbon atoms, and a fluoroalkyl group having 1 to 10 carbon atoms.

6. A polyimide film for a flexible display comprising the polyimide of claim 5.

7. A polyimide substrate for an Oxide TFT or LTPS comprising the polyimide of claim 5.

8. A diamine represented by any one of the following formulae 1b to 1e,

[Formula 1b]

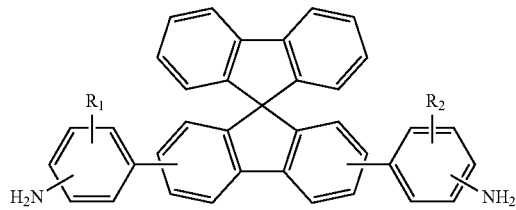

-continued

[Formula 1c]

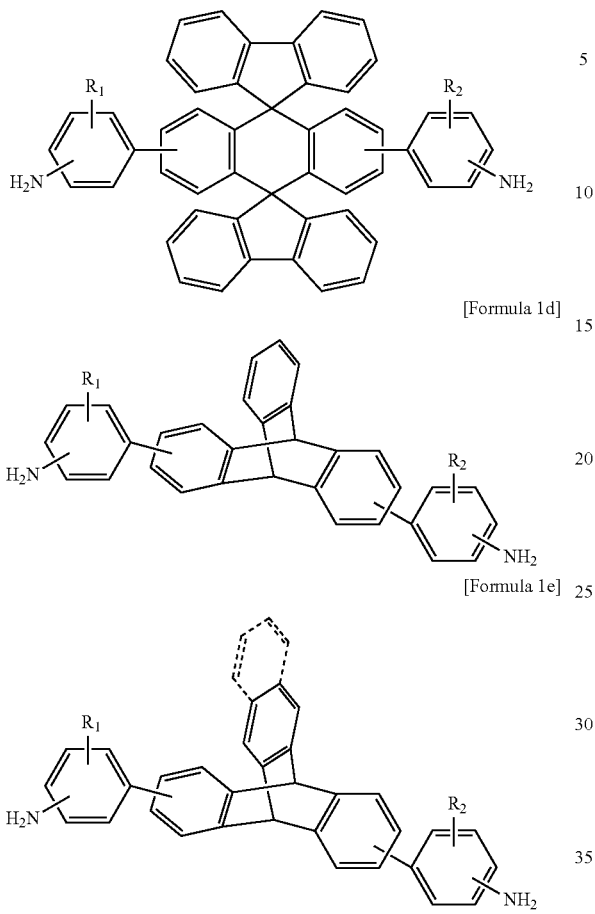

[Formula 1d]

[Formula 1e]

wherein, in formulae 1c to 1e,
$R_1$ and $R_2$ are each independently a hydrogen atom or a substituent selected from a halogen atom, a hydroxyl group (—OH), a thiol group (—SH), a nitro group (—NO$_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, and
wherein in Formula 1b, $R_1$ and $R_2$ are each independently a halogenoalkyl group having 1 to 10 carbon atoms.

9. The polyimide according to claim 1, wherein the composition further comprises a diamine comprising one or more divalent organic group selected from the group consisting of following formulae 4a to 4e:

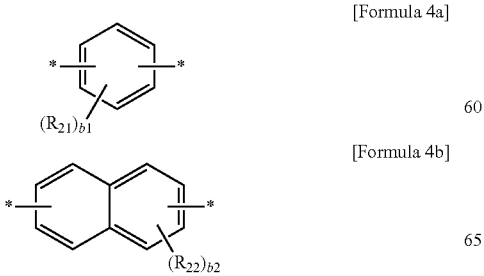

[Formula 4a]

[Formula 4b]

-continued

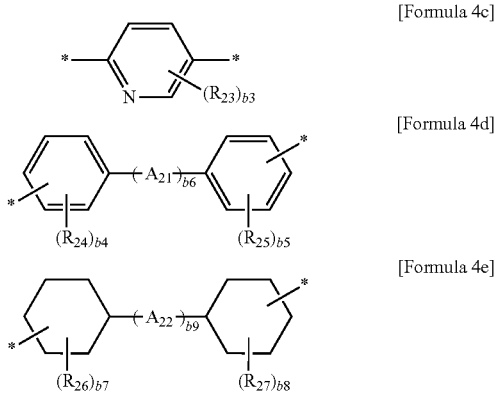

[Formula 4c]

[Formula 4d]

[Formula 4e]

wherein, in formulae 4a to 4e,
$R_{21}$ to $R_{27}$ are each independently selected from an alkyl group having 1 to 10 carbon atoms, a halogen group, a hydroxy group, a carboxyl group, an alkoxy group having 1 to 10 carbon atoms and a fluoroalkyl group having 1 to 10 carbon atoms,
$A_{21}$ and $A_{22}$ are each independently selected from a single bond, —O—, —CR'R"—(wherein R' and R" are each independently selected from a hydrogen atom, an alkyl group having 1 to 10 carbon atoms and a haloalkyl group having 1 to 10 carbon atoms), —C(=O)—, —C(=O)O—, —C(=O)NH—, —S—, —SO—, —SO$_2$-, —O[CH$_2$CH$_2$O]y (wherein y is an integer of 1 to 44), —NH(C=o)NH—, —NH(C=O)O—, a monocyclic or polycyclic cycloalkylene group having 6 to 18 carbon atoms, a monocyclic or polycyclic arylene group having 6 to 18 carbon atoms, and a combination thereof, and
$b_1$, $b_4$ and $b_5$ are each independently an integer of 0 to 4, $b_2$ is an integer of 0 to 6, $b_3$ is an integer of 0 to 3, $b_6$ and $b_9$ are each independently an integer of 0 or 1, and $b_7$ and $b_8$ are each independently an integer of 0 to 10.

10. The polyimide according to claim 1, wherein the diamine comprising one or more divalent organic group is selected from the group consisting of following formulae 5a to 5t,

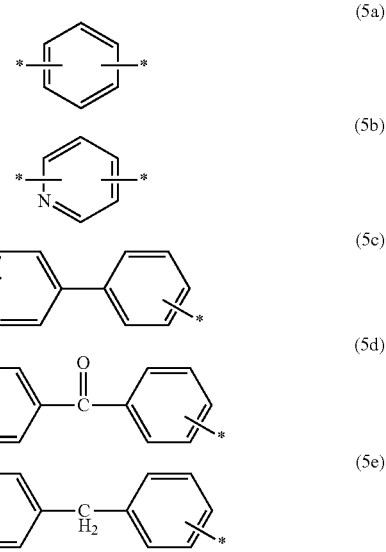

(5a)

(5b)

(5c)

(5d)

(5e)

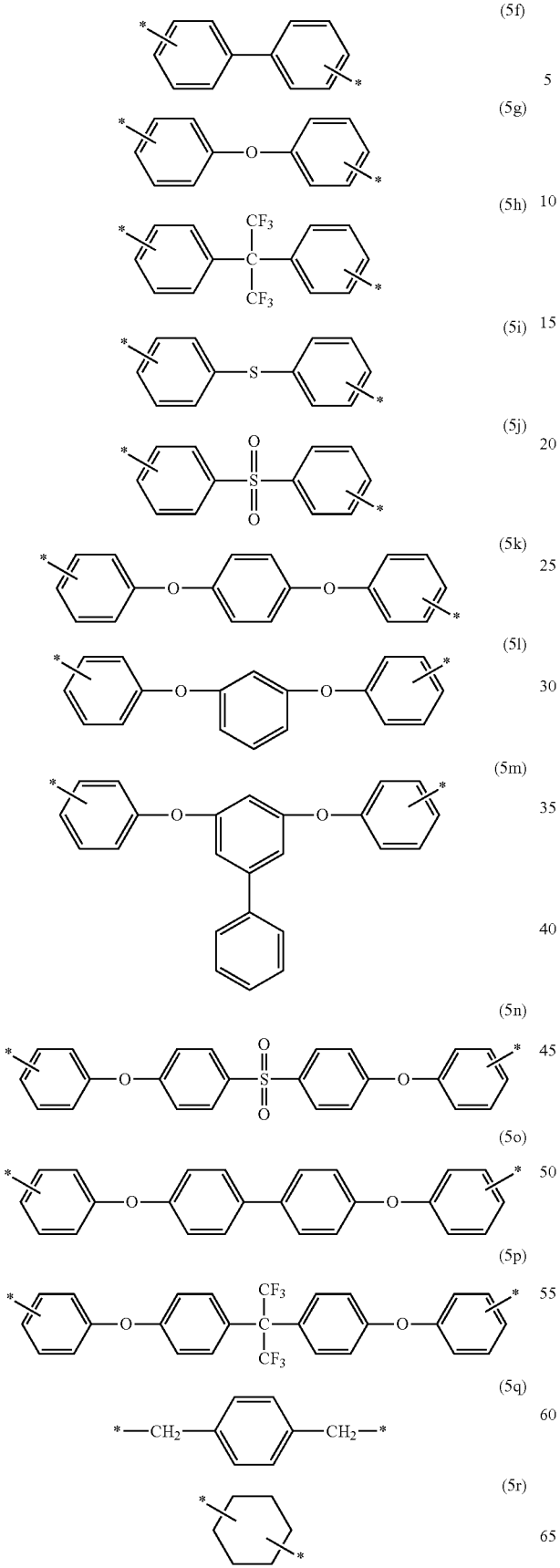

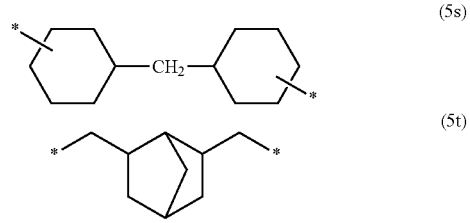

wherein, in formula 5a to 5t, at least one hydrogen atom present in the divalent organic group is unsubstituted or substituted with a substituent selected from a halogen atom selected from —F, —Cl, —Br and —I, a hydroxyl group (—OH), a thiol group (—SH), a nitro group (—$NO_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms.

11. The polyimide according to claim 1, wherein the tetracarboxylic dianhydride comprises one or more tetravalent organic structure selected from the group consisting of tetravalent organic groups represented by the following formulae 2a to 2e:

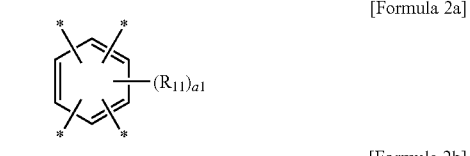

[Formula 2a]

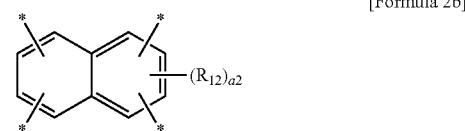

[Formula 2b]

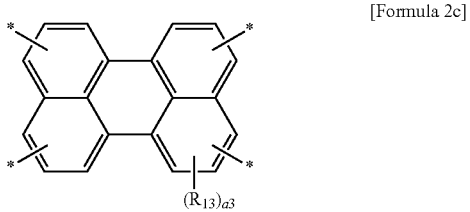

[Formula 2c]

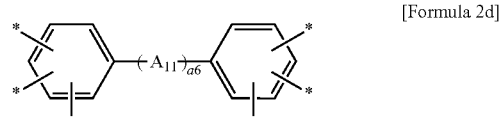

[Formula 2d]

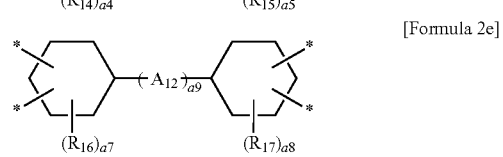

[Formula 2e]

wherein, in formulae 2a to 2e, $R_{11}$ to $R_{17}$ are each independently a hydrogen atom or a substituent selected from a halogen atom, a hydroxyl group (—OH), a thiol group (—SH), a nitro group (—$NO_2$), a cyano group, an alkyl group having 1 to 10 carbon atoms, a halogenoalkoxy group having 1 to 4 carbon atoms, a halogenoalkyl group having 1 to 10 carbon atoms and an aryl group having 6 to 20 carbon atoms, a1 is an integer of 0 to 2, a2 may be an integer of 0 to 4, a3 is an integer of 0 to 8, a4 and a5 are each independently an integer of 0 to 3, a6 and a9 are each independently an integer of 0 to 3, and a7 and a8 are each independently an integer of 0 to 9, and $A_{11}$ and $A_{12}$ are each independently selected from the group consisting of a single bond, —O—, —$CR_{18}R_{19}$-, —C(=O)—, —C(=O)NH—, —S—, —$SO_2$-, a phenylene group and a combination thereof, wherein $R_{18}$ and $R_{19}$ are each independently selected from the group consisting of a hydrogen atom, an alkyl group having 1 to 10 carbon atoms, and a fluoroalkyl group having 1 to 10 carbon atoms.

12. The polyimide according to claim 1, wherein the tetracarboxylic dianhydride comprises a tetravalent organic group selected from the group consisting of the following formulae 3a to 3r in the structure:

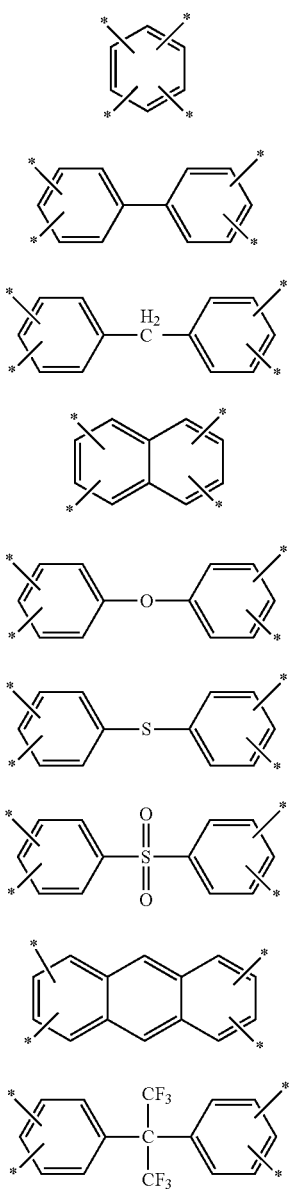
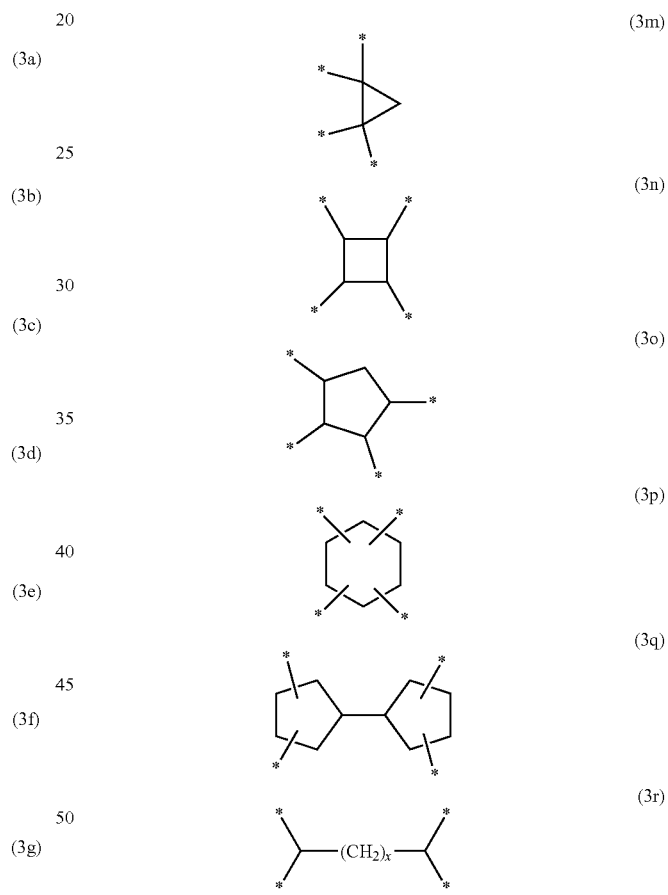

wherein, in formula 31, A2 may be selected from the group consisting of a single bond, —O—, —C(=O)—, —C(=O)NH—, —S—, —$SO_2$—, a phenylene group and a combination thereof and v is an integer of 0 or 1, and in formula 3r, x is an integer of 1 to 10.

13. The polyimide according to claim 1, wherein a molar ratio of a total content of the tetracarboxylic dianhydride to a total content of the diamine is 1:0.99 to 0.99:1.

14. The polyimide according to claim 1, wherein a weight average molecular weight of the polyimide is 10,000 to 200,000 g/mol.

15. The polyimide according to claim 1, wherein a molecular weight distribution of the polyimide is 1.1 to 2.5.

16. A method of preparing the polyimide of claim 1 comprising polymerizing the tetracarboxylic dianhydride with the diamine to form a polymerized product and imidizing the polymerized product.
17. The polyimide according to claim 1, wherein the composition further comprises a diamine of Formula 1a:
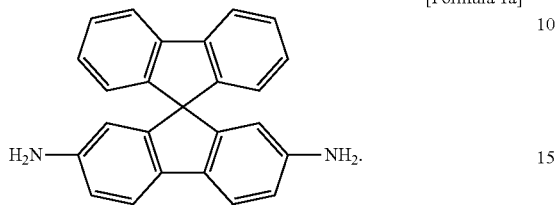
[Formula 1a]
* * * * *